(12) United States Patent
Mach

(10) Patent No.: US 8,714,984 B2
(45) Date of Patent: May 6, 2014

(54) INJECTION SIMULATOR

(75) Inventor: Hung Mach, New York, NY (US)

(73) Assignee: One World Design and Manufacturing Group, LTD, Warren, NJ (US)

( * ) Notice: Subject to any disclaimer, the term of this patent is extended or adjusted under 35 U.S.C. 154(b) by 397 days.

(21) Appl. No.: 13/182,748

(22) Filed: Jul. 14, 2011

(65) Prior Publication Data

US 2012/0015336 A1    Jan. 19, 2012

Related U.S. Application Data

(60) Provisional application No. 61/365,178, filed on Jul. 16, 2010.

(51) Int. Cl.
    *G09B 23/32*    (2006.01)
(52) U.S. Cl.
    USPC .......................... 434/268; 434/267; 434/272

(58) Field of Classification Search
    USPC .......................................... 434/267, 268, 272
    See application file for complete search history.

(56) References Cited

U.S. PATENT DOCUMENTS

| | | | | |
|---|---|---|---|---|
| 8,062,344 | B2 * | 11/2011 | Dorn et al. | 623/1.11 |
| 8,414,609 | B2 * | 4/2013 | List | 606/182 |
| 2002/0052578 | A1 * | 5/2002 | Moller | 604/208 |
| 2010/0196868 | A1 * | 8/2010 | Mourton | 434/272 |

OTHER PUBLICATIONS

Montour, Tracy—Damping Grease—An Economical Approach to Motion and Noise Control, Nye Lubricants, Inc. www.nyelubricants.com, 5 Pages, Not Dated—See Attached.

* cited by examiner

*Primary Examiner* — Benjamin Layno
(74) *Attorney, Agent, or Firm* — Mitchell J. Mehlman, Esq.

(57) ABSTRACT

Injection training devices comprising elements for repeatable and accurate simulation of parenteral injection for training individuals in the administration of one or more medications are provided.

25 Claims, 14 Drawing Sheets

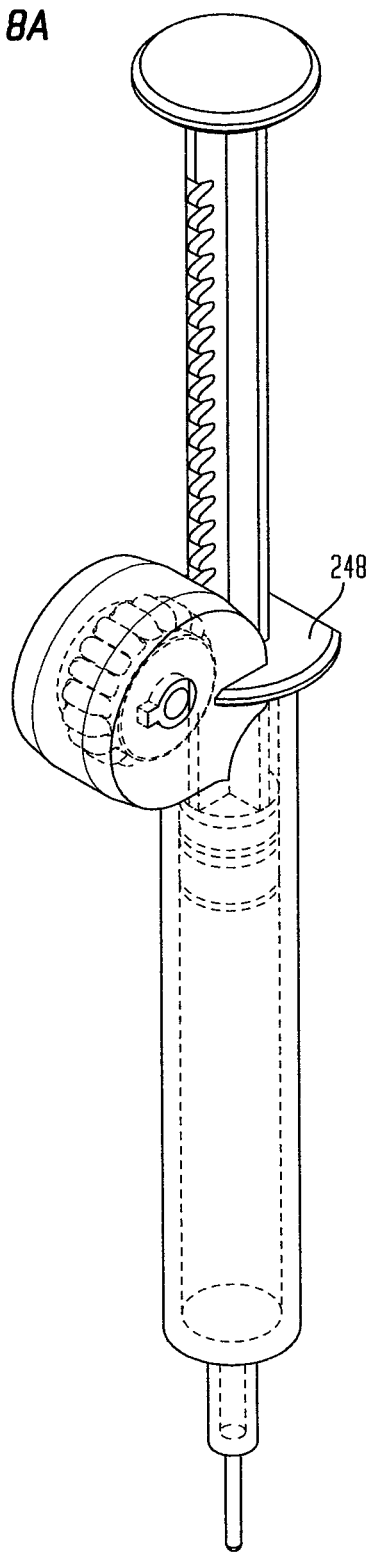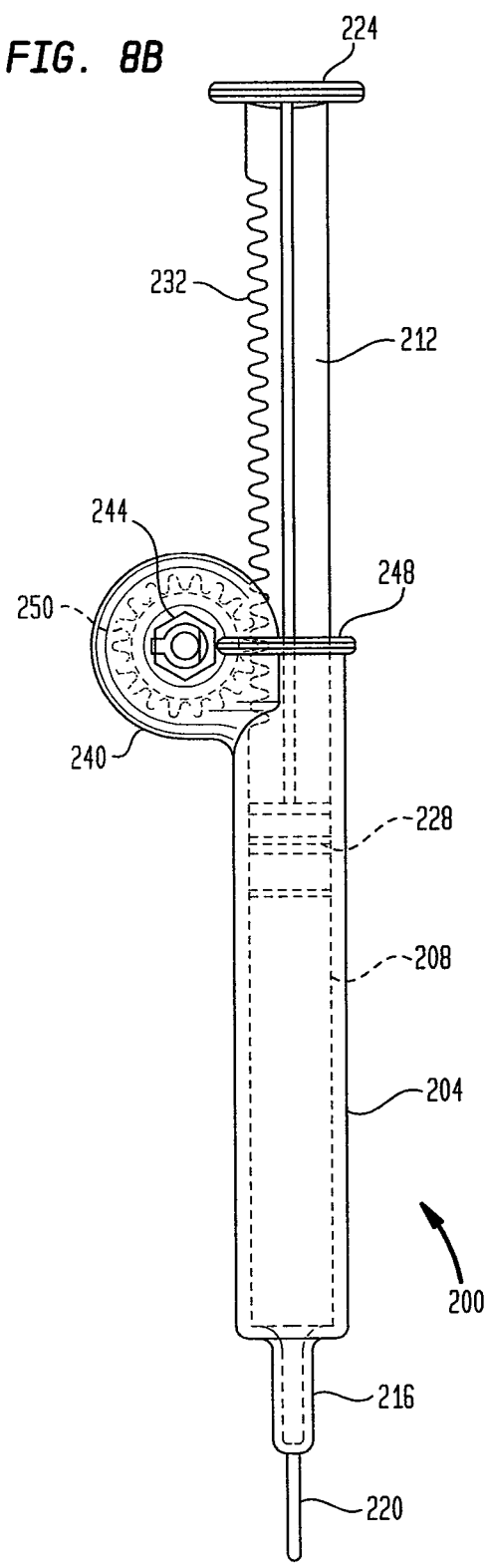

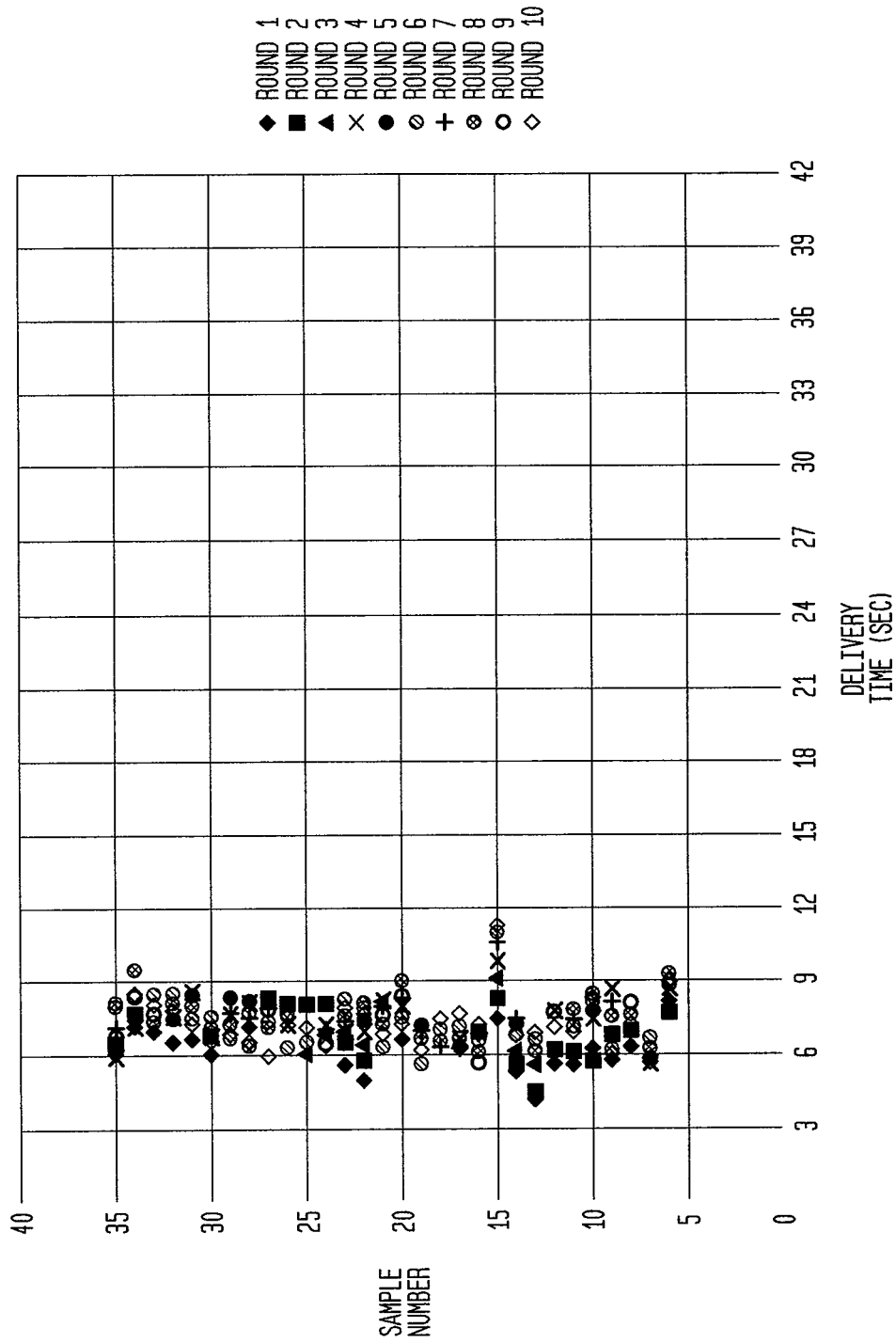

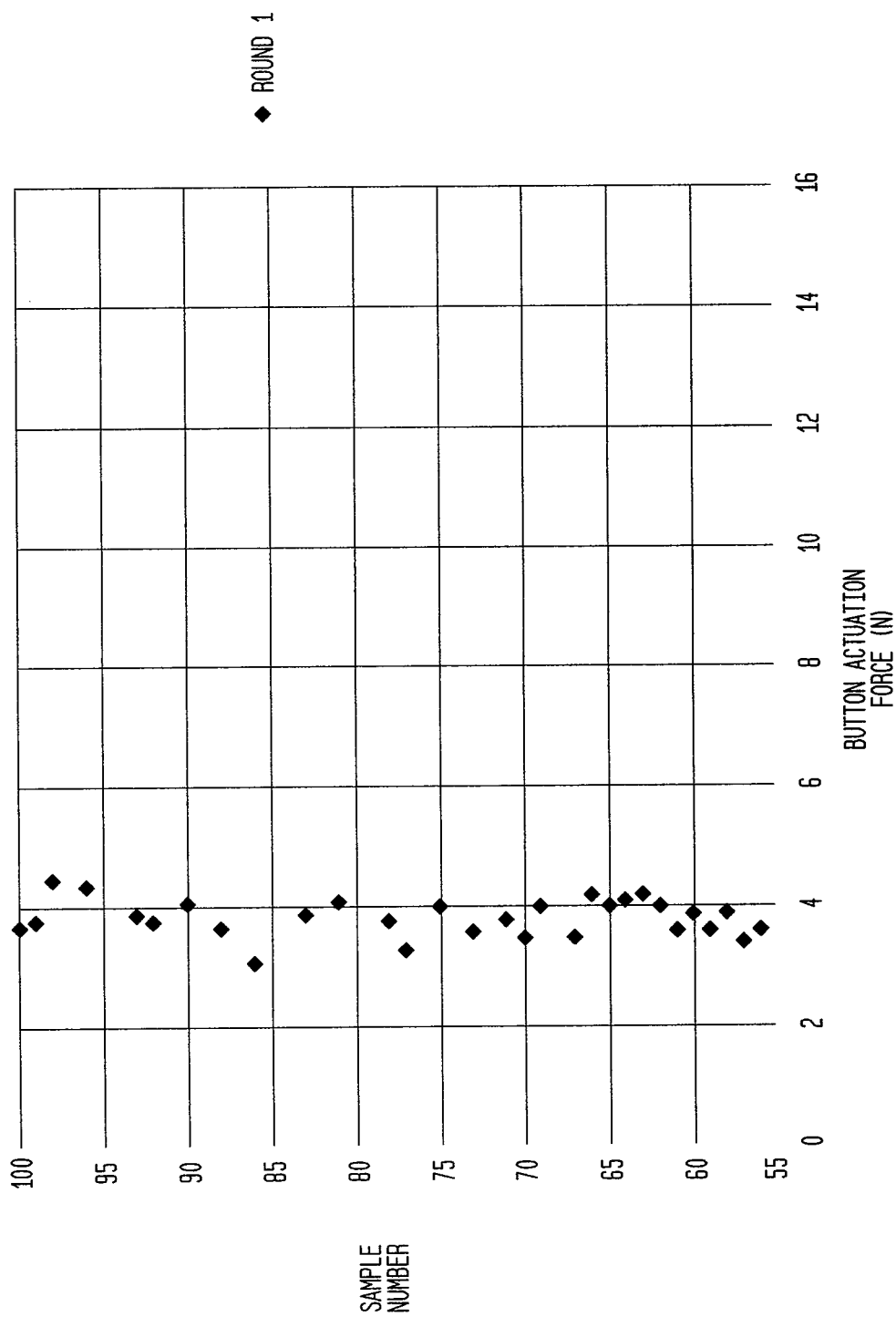

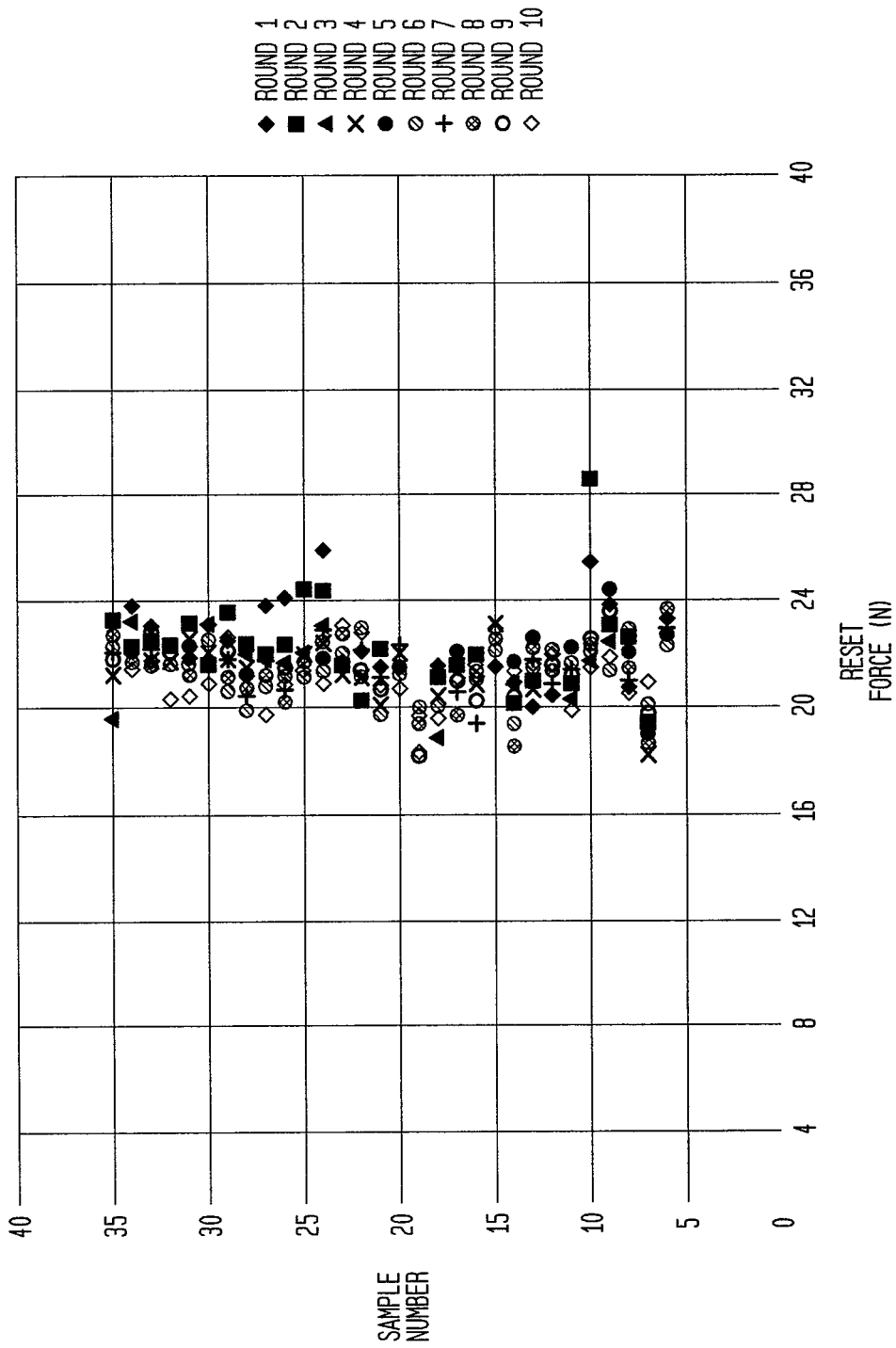

INJECTION SIMULATOR

CROSS-REFERENCE TO RELATED APPLICATION

This application claims priority of U.S. Provisional Application No. 61/365,178, titled "A device that simulates the action of a pre-filled medicine syringe used to teach patients how to operate an actual pre-filled medicine syringe.", filed Jul. 16, 2010, the disclosure of which is incorporated herein by reference in its entirety.

STATEMENT REGARDING FEDERALLY SPONSORED RESEARCH OR DEVELOPMENT

NOT APPLICABLE

REFERENCE TO SEQUENCE LISTING, A TABLE, OR A COMPUTER PROGRAM LISTING COMPACT DISC APPENDIX

NOT APPLICABLE

BACKGROUND

The present invention relates to parenteral injection training devices including devices that simulate an injection time or a resistance of a filled injection device or syringe.

Many people take medications one or more times a day to maintain or improve their health. Often, these medications must be delivered by injection or parenterally, that is, taken into the body or administered in a manner other than through the digestive tract.

If medications are not taken in the proper manner, individual health may be jeopardized. For example, failure to take a complete injection for treatment of diabetes can result in severe health consequences, including death. Non-compliance with a prescribed dose regimen includes patients who fail to properly inject their medication or only inject a portion of their medication.

Further, failure to properly inject medications, particularly in the elderly and the aging population, can result in billions of dollars of unnecessary health care costs because expensive medications can be wasted in the process. That is, an incomplete injection, often leaves expensive or necessary medication in a syringe that is disposed of in the garbage.

An injection (often referred to as a "shot" is an infusion method of putting fluid into the body, usually with a hollow needle and a syringe which is pierced through the skin to a sufficient depth for the material to be forced into the body. An injection follows a parenteral route of administration; that is, administered other than through the digestive tract.

Some medications must be delivered into the body parenterally. It is common for manufacturer's of such medications to provide medication for injection in pre-filled syringes. Common syringes, whether pre-filled, or filled by the patient, manual or auto-injection, typically utilize a hollow needle for delivering a liquid medication from the syringe into the body. Theses medications are typically stored in a cylinder having a hollow needle connected to a cylindrical reservoir and having a plunger for forcing the liquid medication from the reservoir, through the needle, into the body.

When force is applied to the plunger by mechanical means, such as in an auto-injection syringe or manually, by the person administering the injection, the medicine is forced through the needle into the body. There is a resistance caused by the liquid medicine being forced through a needle. The magnitude of the resistance dictates the time that it takes to force all the medicine through the needle and complete the injection.

An auto-injector is a medical device designed to deliver a single dose of a particular, typically life-saving, drug but may be provided for many kinds of drugs.

Most auto-injectors operate as spring-loaded syringes. By design, auto-injectors are easy to use and are intended for self-administration by patients, or administration by untrained personnel. The site of injection depends on the drug loaded, but administration typically is into the arm, thigh or the buttocks. These injectors were initially designed to overcome the hesitation associated with self-administration of a needle-based drug delivery device.

An auto-injector typically keeps the needle tip shielded prior to injection and also may have a safety mechanism to prevent accidental firing (injection). Injection depth can be adjustable or fixed and a function for needle shield removal may be incorporated. By pressing a button, the syringe needle is automatically inserted and the drug is delivered. Once the injection is completed some auto injectors have visual indication to confirm that the full dose has been delivered. Auto-injectors may contain glass syringes, this can make them fragile and contamination can occur. More recently, companies have been making auto-injectors syringes using plastic to prevent this issue.

Patients require training in the operation of a an auto-injector or manual syringe. Known methods of training patients include using an actual auto-injector or manual syringe. These methods are impractical and undesirable because patients would receive multiple or unnecessary injections. While it is possible to use a known injection device without the medication or without a needle, such a simulation would not accurately replicate an actual injection. For example, without liquid medication in the injection device, the patient would inject too quickly because there is no liquid present to resist the force applied to a plunger. Thus, in such a case, a patient would be trained to believe that the injection process is much faster than an actual injection and may, in actual practice, pull the needle out of their skin too early thus receiving an inadequate dose of medication.

Some known training devices simply remove liquid medicine from the actual injection device in order to use the empty unit as an injection trainer. As mentioned above, this approach does not accurately simulate the duration or the force required in an actual injection.

Novel injection training devices that can be reusable and can accurately simulate an injection time or resistance and methods of training for improving patient compliance in parenteral administration of liquid medications are disclosed herein.

SUMMARY OF THE INVENTION

In one aspect of the invention an apparatus can comprise a first gear. The gear can have a first set of gear teeth, an inside surface and a central aperture. The apparatus can have a first stationary drum element and a second stationary drum element that mates with the first stationary drum element and the first gear to form an assembly. The assembly can include a cavity formed between the first and second drum elements and the inside surface of the first gear. The cavity can be substantially filled with a damping grease. The device can also comprise a second gear having a second set of gear teeth. The first and second sets of gear teeth can be fitted to articulate with each other. The device can include an assembly carrier. The carrier comprising one or more supports for mounting the assembly, wherein the one or more supports prevent rotation of the stationary drum elements while said first gear rotates thereby engaging the first set of gear teeth with the second set of gear teeth at a predetermined speed.

In one embodiment of the invention, the first gear can be substantially circular.

In another embodiment of the invention, the second gear can be substantially linear.

In some embodiments of the invention, the damping grease comprises silicone.

In other embodiments of the invention, the damping grease can comprise dimethylpolysiloxane.

In certain embodiments of the invention, the damping grease can have a viscosity between about 900,000 cps and about 1,100,000 cps at 25 degrees C.

In other embodiments of the invention, the gear can have eighteen circumferential teeth located about twenty degrees apart.

In yet other embodiments of the invention, the assembly carrier can be actuated by at least one spring element.

In some embodiments of the invention, the at least one spring element can be stainless steel.

In certain embodiments of the invention, actuating the carrier can produce at least one audible user alert sound.

In certain embodiments of the invention, actuating the carrier can produce a first and a second audible user alert. The first alert can indicate that a simulated injection has started. The second alert can indicate that the simulated injection is complete.

In some embodiments of the invention, the first alert and the second alert can occur at a predetermined time interval.

In some embodiments, the predetermined time interval can be between about 5 seconds and about 15 seconds.

In yet other embodiments the predetermined time interval can be between 3 seconds and 15 minutes.

In another aspect of the invention a method can comprise the steps of: (a) actuating a carrier assembly; the carrier assembly comprising one or more supports for mounting a drum assembly, the drum assembly having a first gear; (b) generating a first user alert sound; (c) rotating the first gear about the drum assembly from an initial position to a final position in a predetermined time; and (d) generating a second user alert sound.

In certain embodiments of this aspect of the invention, the method can further including the step of (e) reloading, wherein the first gear is moved from the final position to the initial position by application of a reset force.

In certain embodiments of the invention, the reset force can be between about 13N and about 18N.

In yet other embodiments of the invention, the method can comprise the further steps of (a) actuating the carrier assembly; the carrier assembly can comprise one or more supports for mounting a drum assembly, the drum assembly can have a first gear (b) generating the first user alert sound (c) rotating the first gear about the drum assembly from the initial position to the final position in the predetermined time; and (d) generating the second user alert sound.

In some embodiments of the invention, the predetermined time can be between about 3 seconds and about 30 seconds.

In other embodiments of the invention, the predetermined time can be between about 5 seconds and about 15 seconds.

In another aspect of the invention, an apparatus can comprise a first gear having a first set of gear teeth, an inside surface and a central aperture. A first stationary drum element and a second stationary drum element that mates with the first stationary drum element and the first gear form an assembly. The assembly can include a cavity formed between the first and second drum elements and the inside surface of the first gear. The cavity can be substantially filled with a damping grease. A second gear can have a second set of gear teeth. The first and second sets of gear teeth can be fitted to articulate with each other. An assembly carrier can comprise one or more supports for mounting the assembly on a syringe housing. The one or more supports can prevent rotation of the stationary drum elements while the first gear rotates and can thereby engage the first set of gear teeth with the second set of gear teeth.

In one embodiment of this aspect of the invention, the first gear can be substantially circular.

In certain embodiments of the invention, the second gear can comprise a plunger.

In some embodiments of the invention, the second gear can be substantially linear.

In certain embodiments of the invention, the damping grease can comprise a polymeric material.

In certain embodiments of the invention, the polymeric material can comprise dimethylpolysiloxane.

BRIEF DESCRIPTION OF THE DRAWINGS

FIGS. 8A and 8B depict several views of another embodiment of the present invention comprising various elements included therein.

FIG. 9 depicts test results of average delivery time vs. actuation cycle by sample number for an embodiment of the present invention.

FIG. 10 depicts test results of trigger button actuation force vs. sample number for an embodiment of the present invention.

FIG. 11 depicts test results of average reset force vs. actuation cycle by sample number for an embodiment of the present invention.

DETAILED DESCRIPTION

As used herein, the terms medicine or medication refers to any material that can be injected into the human body. The terms medicine or medication may be singular or plural and are used interchangeably herein.

As used herein, the terms syringe or injector refer to any device capable of injecting a medicine into the human body.

Figure 1:
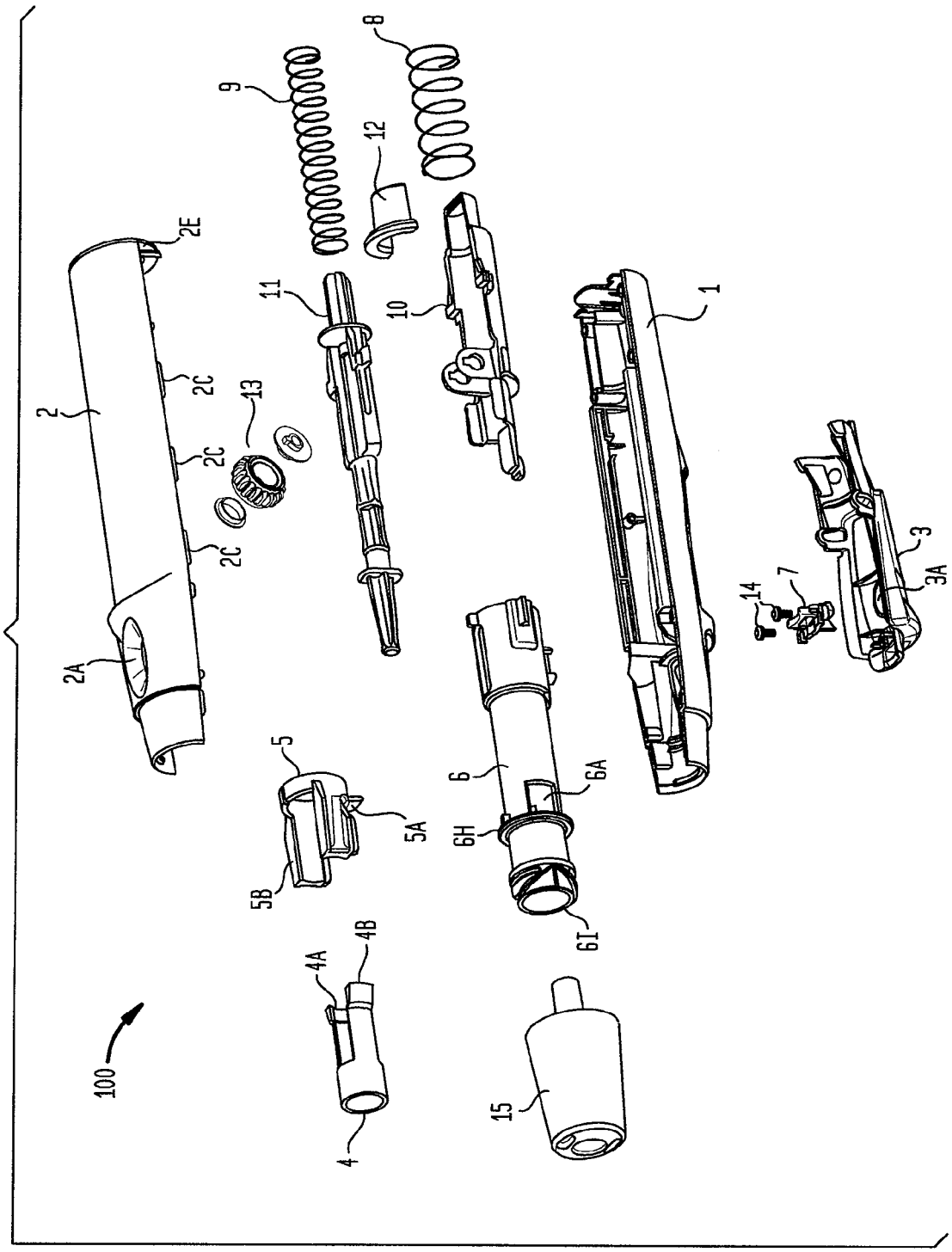
FIG. 1 depicts an isometric exploded view of an injection training device according to one embodiment of the present invention.
Figure 2A:
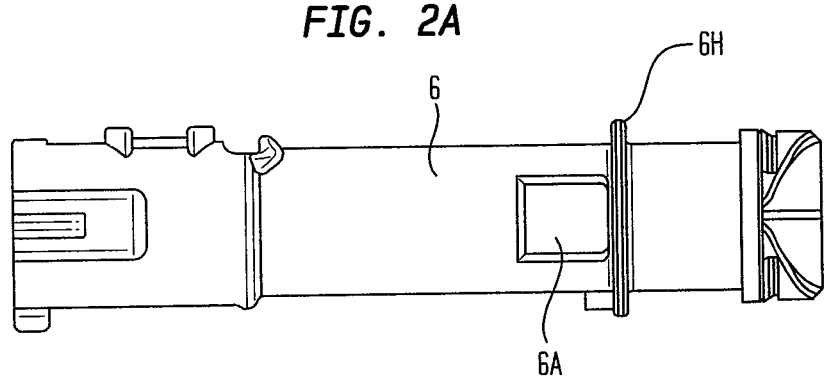
FIGS. 2A through 2E depict several views of a barrel element included in the injection training device of FIG. 1.
Figure 2B:
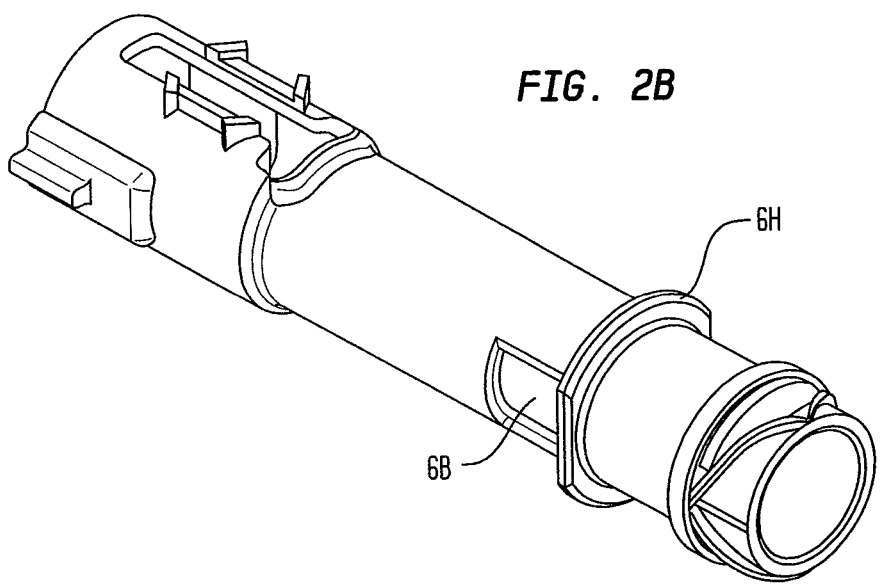
Figure 2C:
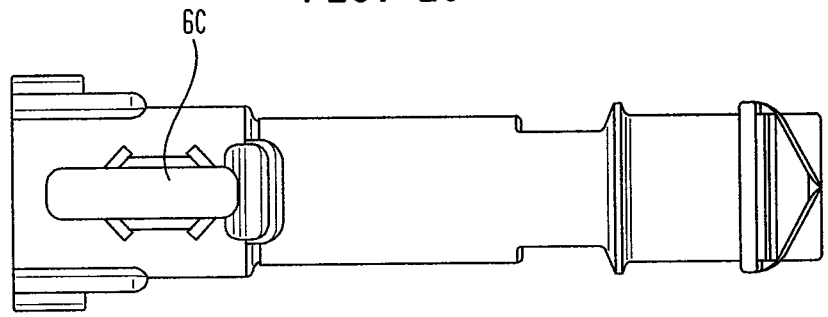
Figure 2D:
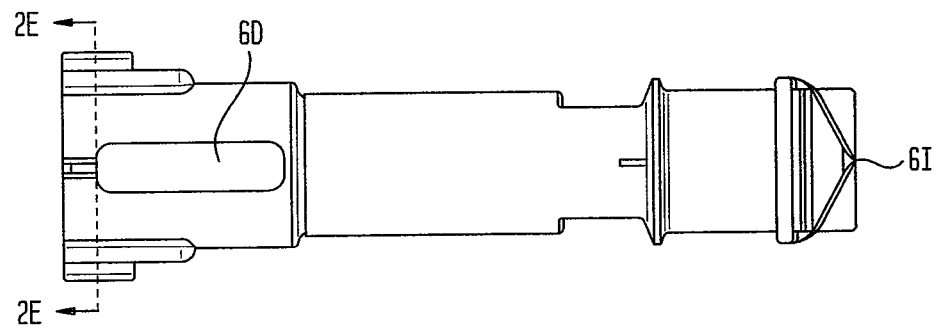
Figure 2E:
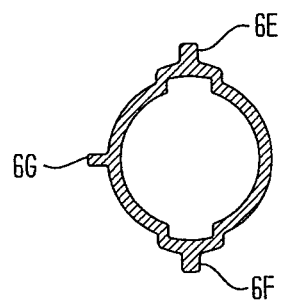

As shown in FIG. 1, injection simulator assembly 100 in accordance with one embodiment of the present invention includes a top case 1 and a bottom case 2. The top and bottom cases include apertures 1A and 2A and can mate through the use of interlocking tabs 2C and slots (not shown) located on the perimeter of both the top case and bottom case, respectively. Top case 1 includes a second aperture 1B for mounting trigger button 3.

Top case 1 and bottom case 2 can be snapped together to lock the assembly and form an enclosure for holding and locating the internal components of the device as described below. When the case is assembled, apertures 1A and 2A are aligned such that an indicator can be viewed through the assembled case as will be discussed below. The top and bottom cases can include ribs 1C and other internal means (not shown), that can be utilized to trap components within the case when the top and bottom cases are snapped together. The top case comprises a rear wall 2E for closure of the assembly and for containing spring element 8 as discussed below.

Components of the present invention can be fabricated from polymers or other structural materials which will be known to one skilled in the art of manufacturing. Like-wise, snap fit designs of many types and manufacturing processes such as, for example, injection molding, compression molding, casting, or machining are well known to those skilled in the art of polymer component manufacturing.

In this embodiment, a trigger button 3 is mounted to top case 1. Trigger button 3 includes aperture 3A and latch attachment 7 which is mounted to substantially perpendicular to trigger button 3 by screws 14. Trigger button 3 is mounted to top case 1 such that when assembled, trigger button 3 can be depressed in the direction of bottom case 2 wherein the latch attachment 7 can lock or can release the injection simulator.

Trigger button 3 and latch attachment 7 can be fabricated from a polymer or other structural material well known in the arts, by for example, injection molding. Screws 14 can be fabricated using materials and manufacturing processes that are well known in the art of manufacturing, such as steel.

As shown in FIGS. 2A-2E, nose barrel 6 can be mounted within top case 1 and bottom case 2. In this embodiment, nose barrel 6 is cylindrically shaped. The nose barrel comprises a front end and a back end, apertures 6A, 6B, 6C, 6D, and tabs 6E, 6F, 6G. Nose barrel 6 includes flange 6H and a contoured nose circularly disposed around the perimeter of the front end 61.

Figure 3:
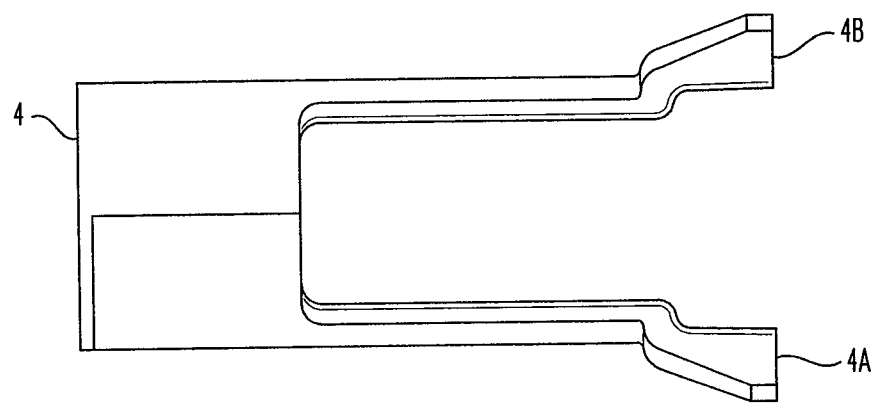
FIG. 3 depicts an isometric view of an interlock element included in the injection training device of FIG. 1.

As shown in FIG. 3, interlock 4, having tabs 4A, 4B can be snap mounted to barrel 6 near the front end of the barrel by disposing tabs 4A and 4B within apertures 6A and 6B.

As shown in FIG. 1, inner lock 5, having tabs 5A, 5B can be slideably mounted on barrel 6 by a utilizing a split ring snap configuration such that tabs 5A, 5B abut tabs 4A, 4B respectively. Inner lock 5 is mounted to barrel such that it is substantially perpendicular to the longitudinal axis of the barrel wherein the inner lock mates in proximity to trigger button aperture 3A.

When top case 1 and bottom case 2 are mated, barrel 6 can be mounted longitudinally within the mated case halves, such that flange 6H is trapped, while tabs 6E and 6F lockably engage top case 1 and tab 6G lockably engages bottom case 2. It is important to recognize that when barrel 6, inner lock 5 and interlock 4 are mated and assembled with top case 1 and bottom case 2, barrel 6 is stationary while interlock 4 and inner lock 5 are slidably mounted. As discussed below, this feature allows for the training device to be triggered only when the interlock 4 is depressed by a user.

A plurality of geometries, barrel configurations, and individual component configurations are contemplated within the scope of the present invention. For example, the barrel 6 can be rectangular or the trigger button 3 can be square.

Figure 4A:
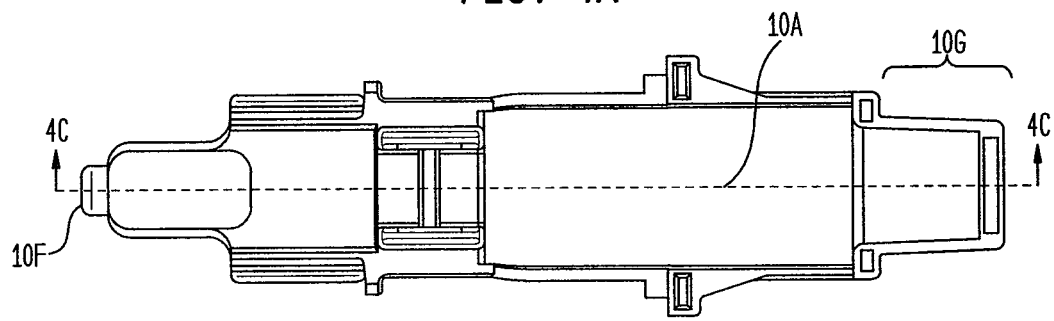
FIGS. 4A through 4C depict several views of a carrier element included in the injection training device of FIG. 1.
Figure 4B:
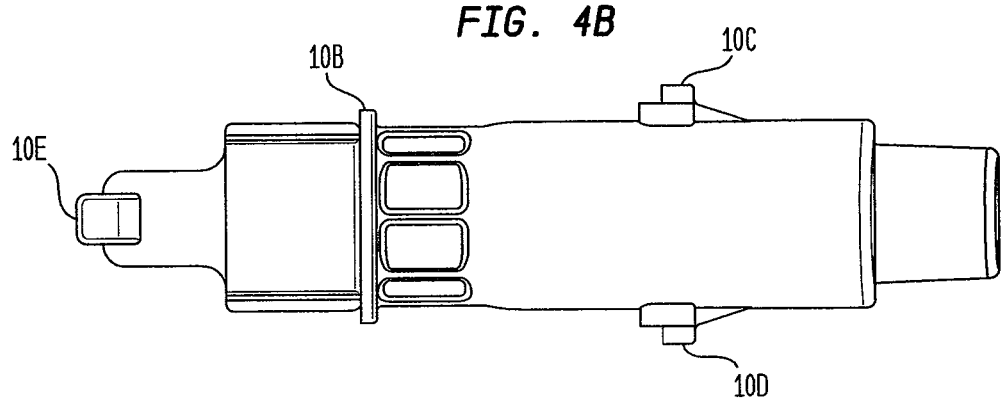
Figure 4C:
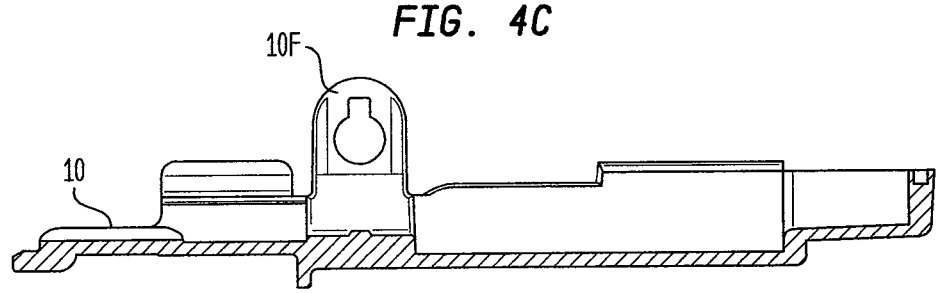

As depicted in FIGS. 4A-4C, carrier 10 comprises cavity 10A, flange 10B, and tabs 10C, 10D, and 10E. Carrier 10 includes a forward end 10F and a rearward end 10G. The carrier can be cylindrical and generally U shaped. The rearward end 10G includes a cavity for containing an inner spring element 9 when it is mated with spring cap 12 as shown in FIG. 1.

The assembly of spring cap 12 with the rearward end 10G creates a cavity for containing inner spring element 9 and an outer diameter for engaging outer spring element 8. Flange 10B and tabs 10C, 10D and 10E engage features in barrel 6 and trigger button 3 such that the carrier is slideably mounted within the closed case (i.e. when top and bottom cases 1 and 2 are in an assembled position).

Carrier 10 has mounting arms 10F for mounting damping gear assembly 13 as discussed below.

Carrier 10 can be molded or fabricated from any suitable durable structural material, for example, a polymeric material. Suitable materials and manufacturing methods will be well known to those skilled in the art of manufacturing engineering polymers.

Figure 5:
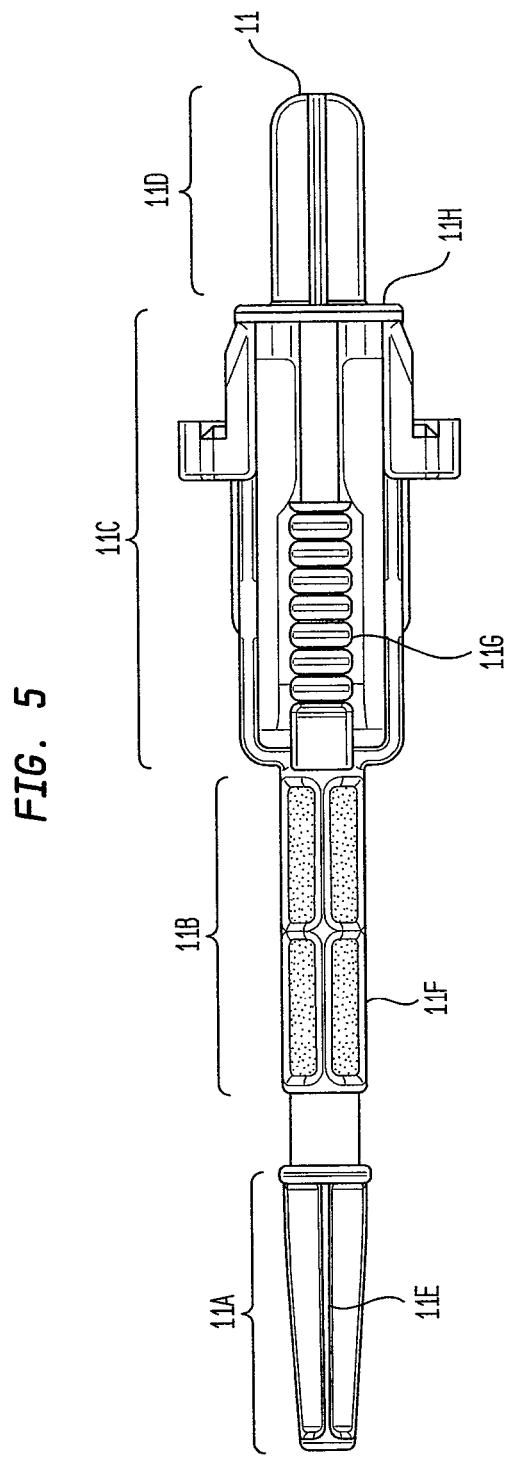
FIG. 5 depicts an isometric view of a plunger element included in the injection training device of FIG. 1.

In this particular embodiment, as shown in FIG. 5, plunger 11 comprises front section 11A, central section 11B, gear track section 11C and a rear section 11D. As shown in FIG. 5, the front section 11A can be tapered and includes an internal feature to simulate the appearance of a hypodermic needle 11E. The central section 11B can be a color, such as yellow, for indicating to the user that the device has been triggered and the simulated injection is complete 11F. During operation, the plunger 11 can translate within the top and bottom case from a first locked and loaded position to a second released injected position wherein section 11B is visible to the user as discussed above.

Figure 6A:
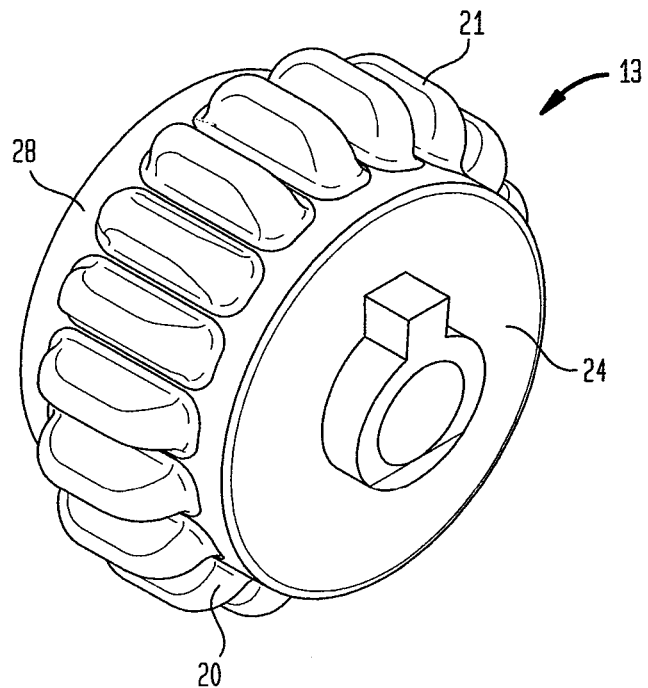
FIGS. 6A and 6B depict several views of a drum and gear assembly included in the injection training device of FIG. 1.
Figure 6B:
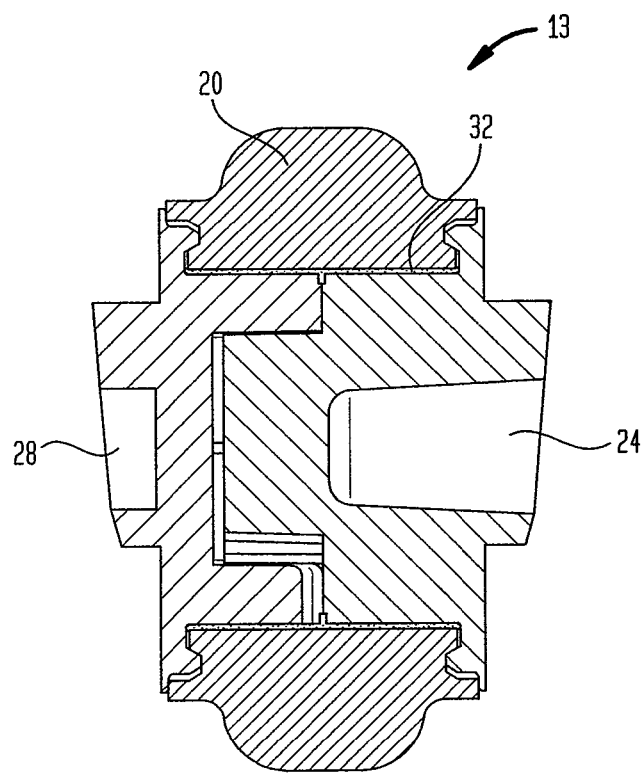

The gear track section 11C of plunger 11 accommodates mounting damping gear assembly 13 (FIGS. 6A-6B). Assembly 14 is mounted to carrier 10 by mounting arms 10F.

As shown in FIGS. 6A-6B, in this particular embodiment, damping gear assembly 14 comprises a substantial circular gear 20 having a central aperture, a first stationary drum 24, a second stationary drum 28 and a damping fluid or grease 32. In this embodiment the circular gear comprises 18 circumferential teeth 21 located about 20 degrees apart. The circumferential gear teeth 21 are designed to mate with gear teeth 11G located along a portion of gear track section 11C (FIG. 5). This feature allows the gear assembly to disengage from the gear track and contact flange 11D to create an audible sound when an injection cycle is complete.

The first and second stationary drums fit together within the central aperture of gear 20 to create a cavity that can be filled with damping grease 32. The gear is free to rotate around the stationary drums. The damping grease in the cavity between the stationary drums and the gear defines a consistent coefficient of friction between the moving parts of the damping gear assembly. This novel mechanism results in a controllable, smooth, predictable and repeatable motion of the device when moving between a first locked and loaded position and a second released injected position.

As mentioned above, the solid components of the present invention can be manufactured using materials and molding methods known to one of skill in the art of manufacturing. The damping grease 32 can be a dimethylpolysiloxane comprising inorganic fillers. One such grease is ASA DG302, manufactured by Asahi of Tokyo, Japan. The speed of the injection device can be modified to suit the needs of a user by, for example, the use of different materials, different gears, different fluids or greases, or different spring elements.

Inner spring element 9 can be mounted on plunger rear section 11D. As explained above, inner spring element can be contained in a longitudinal direction along the long axis of the device between plunger flange 11H and carrier 10. The assembly of spring cap 12 with the rearward end 10G (FIG. 1) creates a cavity for containing inner spring element 9 and an outer diameter for holding outer spring element 8 which can be mounted longitudinally between the spring cap 12 and carrier 10 assembly and rear the rear wall 1E of the top cap when assembled.

Spring elements 8 and 9 may be metallic or non-metallic. A preferred material is stainless steel, however, selection of the material and spring element design will depend on the forces required for each spring to function in accordance with a particular design. The spring elements may be designed to provide more force or less force, thus allowing for a multitude of designs for simulating different injection times and resistances while allowing for reuse and ease of reloading.

Figure 7A:
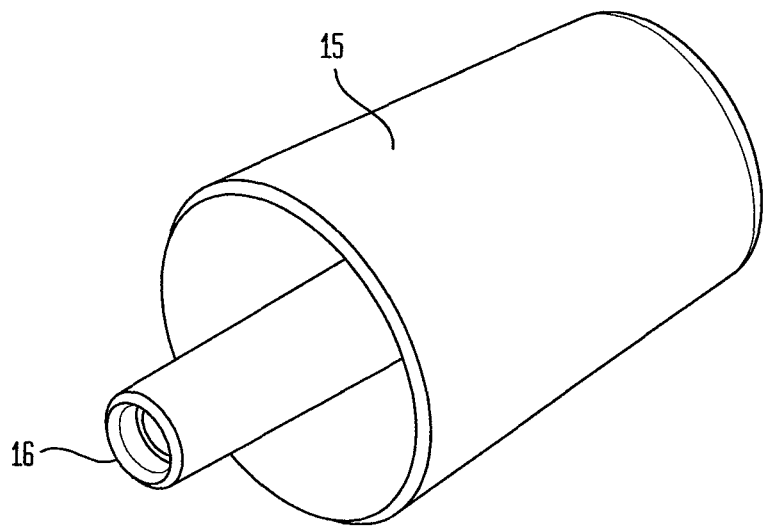
FIGS. 7A and 7B depicts several views of cap and stem elements included in the injection training device of FIG. 1.
Figure 7B:
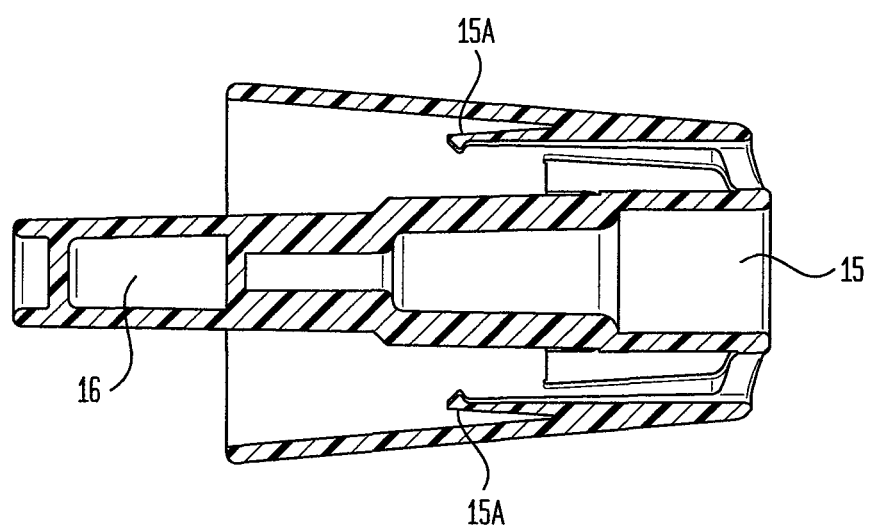

As shown in FIGS. 7A-7B, cap 15 includes stem element 16. Cap 15 can include grippers 15A. The grippers and the cap geometry are fitted to frictionally mount to the end of the device to protect the mechanism and simulate the look and feel of an actual auto-injection syringe. Further, the stem element is sized such that when the device is discharged, the stem element can be used to push the plunger back into a locked and loaded position to reset the device for reuse.

The geometry depicted in this embodiment of the present invention is one of many configurations that can utilize the invention disclosed herein. For example, it is contemplated that the gear track can be substantially linear, circular or spiral for use in various embodiments of the invention.

In operation, a user can remove the cap. The user can observe thorough the apertures in the top and bottom cases that the device is in a loaded or ready position, that is, the device has been reset using the cap to move the plunger into a locked or loaded position. In this loaded position, both spring elements 8 and 9 are compressed, and the damping gear assembly 13 engages a portion of the teeth on the plunger track. When the user depresses the interlock against a potential injection site, such as and arm or thigh, the trigger button can be depressed by the user. If the interlock is not depressed, the training device will remain locked and pressing the trigger will not initiate a training cycle. This feature prevents accidental "injection" and closely simulates actual auto-injectors that are commonly used in the industry.

When the user depresses the trigger button, the spring elements are released and are thus free to act against the plunger or carrier. Depressing the trigger button creates an audible click or snapping sound that can alert a user that the injection process has been initiated. The user can also see movement of the plunger through the apertures in the top and bottom cases.

Because the drum assembly is stationary and has a substantially constant frictional resistance, the spring forces cause the plunger to move in the direction of the interlock and the gear to rotate along the track on the carrier. When the gear rotates beyond the carrier track teeth, the resistance decreases such that the spring forces acting on the plunger causes the gear to contact the plunger flange, thus creating a second audible click which indicates that the injection process has been completed.

As discussed above, the user can also see that a colored, for example, a yellow portion of the plunger is now visible through the apertures in the top and bottom cases. Thus, the user can confirm both audibly or visually when the simulated injection has started and when it has completed.

The time between the start of the simulated or training injection and the completion of the injection can be modified to cover a range of injection times. The injection time required will depend on the specific medication injected and the medical specifications required for such an injection.

Using the training device, the user can repeat the process as often as necessary until the user is trained before administration of medication with an actual syringe or auto-injector. It is contemplated that the injection time can be between about 1 second and about 15 minutes.

In this way, a patient will have less of a tendency to inject a medication too quickly, too slowly or not completely, all of which can be dangerous or costly to the patient. For example, removal of a syringe before completion of the actual injection may cause the patient to receive a lower dosage than necessary and waste medicine that may remain in the syringe or may squirt out of the syringe but not into the body.

In another embodiment of the invention, as shown in FIGS. 8A-8B, the simulation device may be adapted to simulate a manual injection rather than an automated injection.

In this embodiment of the present invention, injection simulator 200 comprises syringe body 204. The body includes cavity 208 adapted to accept plunger 212. The body can include a tapered region 216 to accept a simulated needle 220. The plunger 212 has a top end 224 having an injection tab and a bottom end 228 adapted to fit the body. The plunger comprises a linear gear track 232 disposed along a portion of the plunger.

Injection training device 200 includes housing 240. Damping gear assembly 244 is mounted within the housing an can be connected to syringe body flange 248. The housing can be a separate component or molded with the body as one or more pieces. As shown in FIG. 8A-8B, in this particular embodiment, damping gear assembly 244 comprises a substantial circular gear 250 having a central aperture, a first stationary drum, a second stationary drum and a damping fluid or grease substantially similar to damping assembly 13 as described above in another embodiment of the present invention and depicted in FIGS. 1, 6A and 6B. The circular gear teeth 228, are designed to mate with linear gear track 232.

The first and second stationary drums fit together within the central aperture of circular gear 244 to create a cavity that can be filled with a damping grease. The circular gear is free to rotate about the stationary drums. The damping grease in the cavity between the stationary drums and the circular gear defines a consistent coefficient of friction between the moving parts of the damping gear assembly. This mechanism results in a smooth, predictable and repeatable motion of the device when moving between a first pre-injection position and a second post-injection position.

As mentioned above, the components can be manufactured using materials and manufacturing methods known to one of skill in the art of manufacturing. The damping grease can be a dimethylpolysiloxane comprising inorganic fillers.

The speed of the injection device or the resistance of the plunger to an injection force can be modified to suit the needs of a user by, for example, the use of different gear sizes, different fluids or greases, or different plunger materials.

In practice, when the user depresses the plunger, the plunger moves within the syringe body. The damping gear assembly controls the rate of motion and acts to inform or train the user as to the look and feel of an actual injection. Because the device may be reset by pulling the plunger in the opposite direction of the injection direction, the user can practice injection at a predetermined rate until the user is trained.

For the purpose of patient training and compliance, this device is far superior to using an actual syringe because an actual empty syringe does not provide resistance similar to an actual injection. Further, many syringes are designed for one time use so that the plunger components may wear out after one or more injections and would fail to provide accurate simulation of an injection in which a fluid usually fills all or part of the syringe body.

Ease and consistency of use are important factors in achieving patient compliance, particularly for very old or very young patients who may not have sufficient strength to operate a training device.

FIG. 9 depicts a graphical plot of the average delivery time for one particular embodiment of the present invention, that is, the time between the start of the simulated injection and the end of the injection. Ten rounds of testing were performed, each round having ten actuation cycles. The range of average delivery times was between about 4 seconds and about 11 seconds. The average delivery time can be designed to meet a range of delivery time requirements, depending on the needs of a particular user.

FIG. 10 depicts the average button actuation force vs. actuation cycle. It can be seen that between test "firings" 56-100 the force required to actuate the device was in the range of 3-5 N. This level of force represents an easily achieved and repeatable level of force for many types of patients.

FIG. 11 depicts the average reset for vs. actuation cycle for ten rounds of testing in which ten actuations were performed for each round. The reset force was generally in the range of 20-24 N as shown in the graph.

Figure 12A:
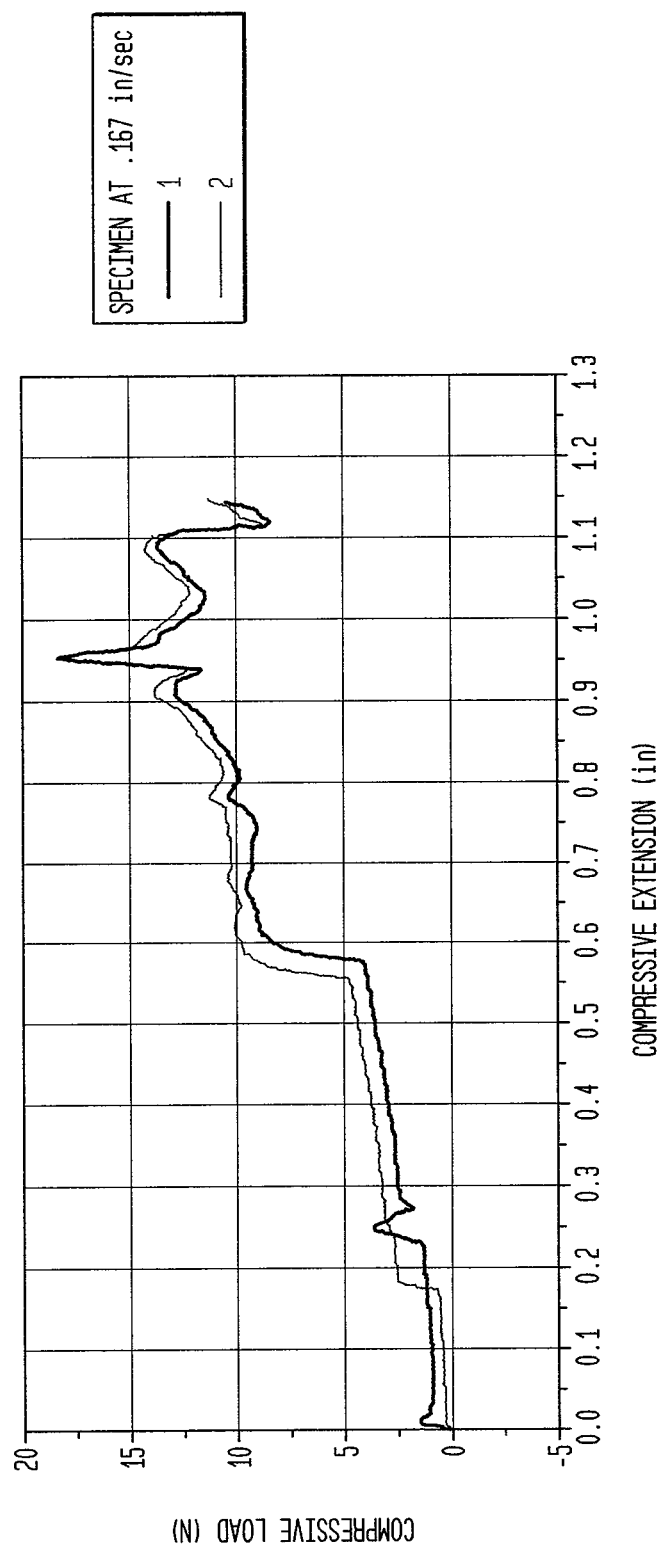
FIGS. 12A and 12B depict test results of reset force vs. reset speed for two samples of an embodiment of the present invention.
Figure 12B:
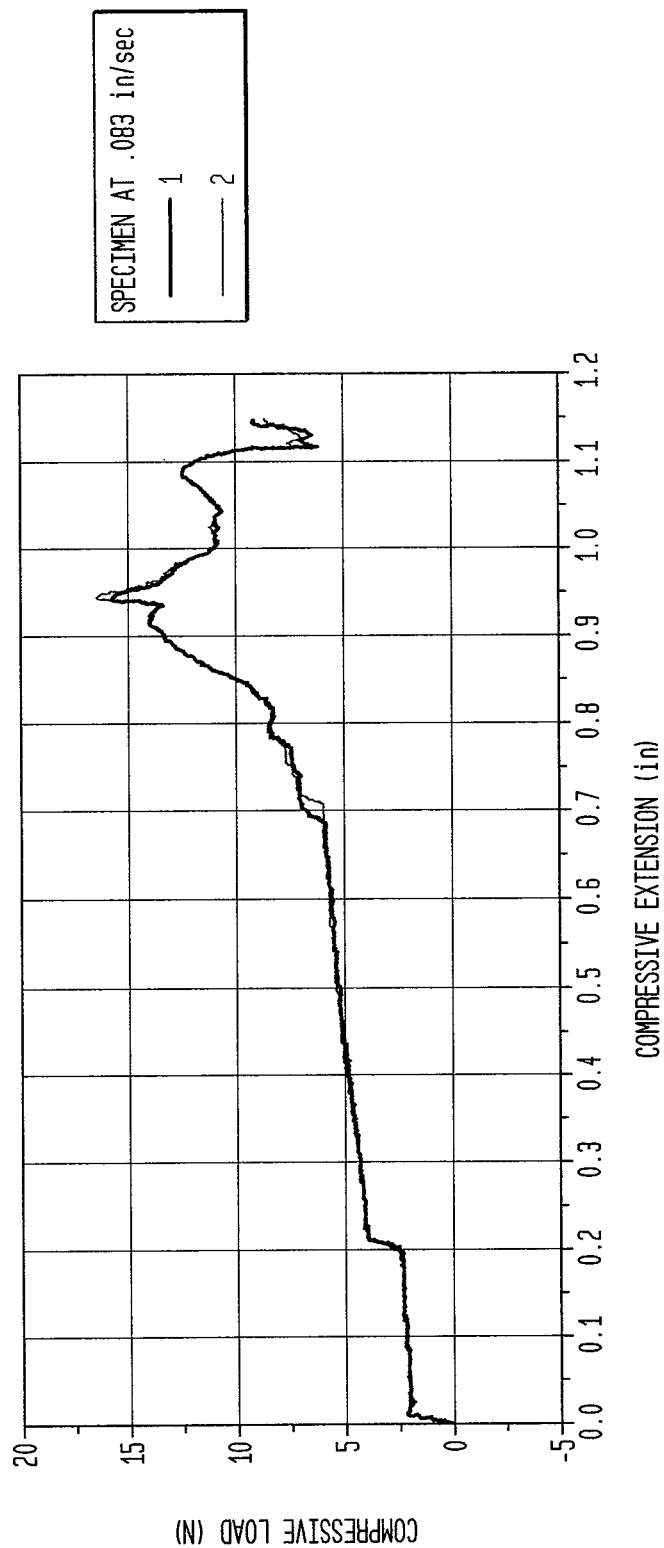

As shown in FIGS. 12 and 12A, the compressive load is plotted for resetting the device at 2 different speeds. Two rounds of testing were conducted on individual samples at 0.167 inches/second and at 0.083 inches/second, respectively (FIGS. 12A and 12B). The mean reset force under these conditions was about 18N at 0.167 inches/second and 16N at 0.083 inches/second. Again, the results indicate that the training device reset force is consistent, repeatable and manageable for a wide range of patients. As expected, resetting the device at a faster rate requires slightly more force.

As will also be appreciated, a significant benefit of the present invention includes the repeatability of the device for training patients to inject one or more medicines and the ability to change the design to accommodate different injection speeds.

Although the invention herein has been described with reference to particular embodiments, it is to be understood that these embodiments are merely illustrative embodiments and that other arrangements may be devised without departing from the spirit and scope of the present invention as defined by the disclosure herein.

What is claimed is:

1. An apparatus comprising:
   (a) a first gear having a first set of gear teeth, an inside surface and a central aperture;
   (b) a first stationary drum element;
   (c) a second stationary drum element that mates with said first stationary drum element and said first gear forming an assembly; said assembly including a cavity between said first and second drum elements and said inside surface of said first gear, said cavity being substantially filled with a damping material;
   (d) a second gear; said second gear having a second set of gear teeth; said first set and said second set of gear teeth being fitted to articulate with each other;
   (e) an assembly carrier; said carrier comprising one or more supports for mounting said assembly, wherein said one or more supports prevent rotation of said stationary drum elements while said first gear rotates thereby engaging said first set of gear teeth with said second set of gear teeth at a predetermined speed.

2. The apparatus of claim 1, wherein said first gear is substantially circular.

3. The apparatus of claim 2, wherein said gear has eighteen circumferential teeth, wherein said teeth are located about twenty degrees apart from each other.

4. The apparatus of claim 1, wherein said second gear is substantially linear.

5. The apparatus of claim 1, wherein said damping material comprises silicone.

6. The apparatus of claim 5, wherein said damping material comprises dimethylpolysiloxane.

7. The apparatus of claim 1, wherein said damping material has a viscosity between about 900,000 cps and about 1,100,000 cps at 25 degrees C.

8. The apparatus of claim 1, wherein the assembly carrier is actuated by at least one spring element.

9. The apparatus of claim 8, wherein said at least one spring element is stainless steel.

10. The apparatus of claim 8, wherein actuating said carrier produces at least one audible user alert.

11. The apparatus of claim 10, wherein actuating said carrier produces a first user alert sound and a second user alert sound; said first user alert sound indicating to a user that a simulated injection has started; said second user alert sound indicating to said user that said simulated injection is complete.

12. The apparatus of claim 11, wherein said user first alert sound and said second user alert sound occur at a predetermined time interval.

13. The apparatus of claim 12, wherein said time interval between the first alert sound and the second alert sound is between about 3 seconds and about 15 minutes.

14. A method of operating an injection simulator comprising:
   (a) actuating a carrier assembly; said carrier assembly comprising one or more supports for mounting a drum assembly, said drum assembly having a first gear;
   (b) generating a first user alert sound indicating that a simulated injection process has been initiated;
   (c) rotating said first gear about said drum assembly from an initial position to a final position in a predetermined time; and
   (d) generating a second user alert sound indicating that said simulated injection process has been completed.

15. The method of claim 14, further including the step of:
   (e) reloading, wherein said first gear is moved from said final position to said initial position by application of a reset force.

16. The method of claim 15, wherein said reset force is between about 13N and about 18N.

17. The method of claim 15, further comprising the steps of:
   (f) actuating said carrier assembly; said carrier assembly comprising a one or more supports for mounting a drum assembly, said drum assembly having a first gear;
   (g) generating said first user alert sound indicating that said simulated injection process has been initiated;
   (h) rotating said first gear about said drum assembly from said initial position to said final position in said predetermined time; and
   (i) generating said second user alert sound indicating that said simulated injection process has been completed.

18. The method of claim 14, wherein said predetermined time is between about 3 seconds and about 15 minutes.

19. The method of claim 18, wherein said predetermined time is between about 5 seconds and about 15 seconds.

20. An apparatus comprising:
(a) a first gear having a first set of gear teeth, an inside surface and a central aperture;
(b) a first stationary drum element;
(c) a second stationary drum element that mates with said first stationary drum element and said first gear to form an assembly; said assembly including a cavity formed between said first and second drum elements and said inside surface of said first gear, said cavity being substantially filled with a damping grease;
(d) a second gear; said second having a second set of gear teeth; said first and second sets of gear teeth being fitting to articulate with each other;
(e) an assembly carrier; said carrier comprising a one or more supports for mounting said assembly on a syringe housing, wherein said one or more supports prevent rotation of said stationary drum elements while said first gear rotates thereby engaging said first set of gear teeth with said second set of gear teeth.

21. The apparatus of claim 20, wherein said first gear is substantially circular.

22. The apparatus of claim 21, wherein said second gear comprises a plunger.

23. The apparatus of claim 22, wherein said second gear is substantially linear.

24. The apparatus of claim 20, wherein said damping grease comprises a polymeric damping material.

25. The apparatus of claim 24, wherein said polymeric damping material comprises dimethylpolysiloxane.

* * * * *